United States Patent
Van Der Waal et al.

(10) Patent No.: US 10,138,184 B2
(45) Date of Patent: *Nov. 27, 2018

(54) CONTINUOUS PROCESS FOR PREPARING ETHYLENE GLYCOL FROM A CARBOHYDRATE SOURCE

(71) Applicant: AVANTIUM KNOWLEDGE CENTRE B.V., Amsterdam (NL)

(72) Inventors: Jan Cornelis Van Der Waal, Amsterdam (NL); Gerardus Johannes Maria Gruter, Amsterdam (NL)

(73) Assignee: Avantium Knowledge Centre B.V., Amsterdam (NL)

( * ) Notice: Subject to any disclaimer, the term of this patent is extended or adjusted under 35 U.S.C. 154(b) by 0 days.

This patent is subject to a terminal disclaimer.

(21) Appl. No.: 15/543,137

(22) PCT Filed: Jan. 13, 2016

(86) PCT No.: PCT/NL2016/050029
§ 371 (c)(1),
(2) Date: Jul. 12, 2017

(87) PCT Pub. No.: WO2016/114661
PCT Pub. Date: Jul. 21, 2016

(65) Prior Publication Data
US 2018/0002259 A1 Jan. 4, 2018

(30) Foreign Application Priority Data

Jan. 13, 2015 (NL) ...................... 2014121

(51) Int. Cl.
C07C 29/74 (2006.01)
B01J 19/00 (2006.01)
C07C 29/132 (2006.01)
C07B 31/00 (2006.01)
C07C 31/20 (2006.01)

(52) U.S. Cl.
CPC ......... *C07C 29/132* (2013.01); *B01J 19/0066* (2013.01); *C07B 31/00* (2013.01); *C07C 31/202* (2013.01); *B01J 2219/00033* (2013.01); *C07C 2523/30* (2013.01); *C07C 2523/89* (2013.01)

(58) Field of Classification Search
CPC ..... C07C 29/74; C07C 29/132; B01J 19/0066
USPC ........................................................ 568/863
See application file for complete search history.

(56) References Cited

U.S. PATENT DOCUMENTS

| 2,360,685 | A | 10/1944 | Jensen |
| 5,425,853 | A | 6/1995 | Berg |
| 6,620,292 | B2 | 9/2003 | Wingerson |
| 8,222,464 | B2 * | 7/2012 | Kalnes ................ C07C 29/132 568/852 |
| 9,399,610 | B2 † | 7/2016 | Schreck |
| 2011/0313208 | A1 | 12/2011 | Kalnes et al. |
| 2011/0313209 | A1 | 12/2011 | Kalnes et al. |
| 2012/0172633 | A1 | 7/2012 | Zhang |
| 2017/0362146 | A1 | 12/2017 | Van Der Waal |

FOREIGN PATENT DOCUMENTS

| CN | 101768050 A | 7/2010 |
| CN | 102643165 A | 8/2012 |
| CN | 102731255 A | 10/2012 |
| CN | 103420797 A | 12/2013 |
| WO | 20130015955 A2 | 1/2013 |
| WO | 2014161852 A1 † | 10/2014 |
| WO | 20140173973 A1 | 10/2014 |
| WO | 2015154258 A1 † | 10/2015 |
| WO | 2016114658 A1 | 7/2016 |
| WO | 2016114659 A1 | 7/2016 |
| WO | 2016114660 A1 | 7/2016 |

OTHER PUBLICATIONS

International Search Report of Application No. PCT/NL2016/050029 dated Jun. 2, 2016.
Ji, N. et al., "Catalytic conversion of cellulose into ethylene glycol over supported carbide catalysts", Catalysis Today, Sep. 30, 2009, pp. 77-85, vol. 147, No. 2, Elsevier, NL.
International Search Report of Application No. PCT/NL2016/050028 dated Jun. 6, 2016.

(Continued)

*Primary Examiner* — Sikarl A Witherspoon
(74) *Attorney, Agent, or Firm* — Thomas|Horstemeyer, LLP

(57) ABSTRACT

Ethylene glycol is prepared from a carbohydrate source by reaction of the carbohydrate source with hydrogen in a continuous process, wherein hydrogen, the carbohydrate source and a liquid diluent are continuously fed into a continuous stirred tank reactor wherein a catalyst system is present, which catalyst system comprises a tungsten compound and at least one hydrogenolysis metal selected from the groups 8, 9 or 10 of the Periodic Table of the Elements, to achieve the reaction between the carbohydrate source and hydrogen to ethylene glycol;

wherein continuously a product mixture comprising ethylene glycol and diluent is removed from the continuous stirred tank reactor; and wherein continuously or periodically further at least a tungsten compound is added to the continuous stirred tank reactor (CSTR).

24 Claims, No Drawings

(56) References Cited

OTHER PUBLICATIONS

Zhao et al., Guanhong et al., "Catalytic Conversion of Concentrated Glucose to Ethylene Glycol with Semicontinuous Reaction System", Ind. Eng. Chem. Res., USA, 2013, vol. 52, pp. 9566-9572.
Ooms, et al. Conversion of sugars to ethylene glycol with nickel tungsten carbide in a fed-batch reactor: high productivity and reaction network elucidation, Green Chem. 2014 vol. 16, pp. 695.†

\* cited by examiner
† cited by third party

CONTINUOUS PROCESS FOR PREPARING ETHYLENE GLYCOL FROM A CARBOHYDRATE SOURCE

CROSS-REFERENCE TO RELATED APPLICATION

This application is the National Stage of International Application No. PCT/NL2016/050029, filed 13 Jan. 2016, which claims the benefit of and priority to NL Application No. 2014121, having the title "Continuous Process For Preparing Ethylene Glycol From A Carbohydrate Source," filed on 13 Jan. 2015, the entire disclosures of which are incorporated by reference in their entireties as if fully set forth herein.

TECHNICAL FIELD

The present invention relates to a continuous process for the preparation of ethylene glycol from a carbohydrate source. In particular it relates to a process for preparing ethylene glycol from a sustainable carbohydrate resource using a specific catalyst system.

BACKGROUND

The catalytic conversion of carbohydrates from a sustainable resource to valuable chemicals such as alkylene glycols has gained interest. Alkylene glycols are interesting chemicals that find application in the preparation of polyesters, such as poly(alkylene terephthalate), poly(alkylene naphthenate) or poly(alkylene furandicarboxylate). Further applications of alkylene glycols, in particular ethylene glycol include their use as anti-freeze. By enabling the preparation of such chemicals from sustainable resources, the dependence of fossil fuel resources is reduced. Since there is a desire to reduce the dependence of fossil fuels there is a growing need for sustainable resources for the production of alkylene glycols such as ethylene glycol.

In U.S. Pat. No. 7,960,594 a process is described wherein ethylene glycol is produced from cellulose. This process involves catalytic degradation and hydrogenation reactions under hydrothermal conditions. More in particular, the process is carried out by contacting cellulose at elevated temperature and pressure with a catalyst system comprising two sorts of active components in the presence of hydrogen. The first active component comprises tungsten or molybdenum in its metallic state or its carbide, nitride or phosphide. The second component is selected from the hydrogenation metals from Groups 8, 9 and 10 of the Periodic Table of Elements, and includes cobalt, nickel, ruthenium, rhodium, palladium, iridium and platinum. In experiments the catalysts compounds were used on a carrier, such as activated carbon. Moreover, it appears that the reaction conditions that result in satisfactory yields include a temperature of 220-250° C. and a hydrogen pressure of 3 to 7 MPa (measured at room temperature). When a 1% wtwt slurry of cellulose is subjected to these compounds for 30 minutes, ethylene glycol is obtained in yields of up to 69%. However, it also appears that when the reaction is continued for a prolonged period the ethylene glycol yield reduces.

This reaction has been further studied on catalyst systems that contain nickel and tungsten on a carrier. There it has been found that nickel and tungsten are leached into the solution during the reaction, which accounts for the gradual deterioration of the catalyst performance (cf. Na Ji et al., Chem Sus Chem, 2012, 5, 939-944). The leaching of tungsten and other metals has been confirmed in the study reported in M. Zheng et al., Chin. J. Catal., 35 (2014) 602-613. The latter document also discloses that in addition to ethylene glycol different by-products are obtained, including 1,2-propylene glycol, erythritol, glycerol, mannitol and sorbitol.

US 2011/0312488 describes a catalyst system for the generation of alkylene glycols from a carbohydrate as a potential alternative for a catalyst comprising the metal components in the elemental state; this catalyst system comprises at least one metal with an oxidation state of at least +2. More in particular this US application discloses a catalyst system comprising a first metal component with an oxidation state of at least +2 and a hydrogenation component. The hydrogenation component can be selected from a wide range of metals in any oxidation state, including in the elemental state. The hydrogenation component may in particular comprise an active metal component selected from the group consisting of Pt, Pd, Ru, Rh, Ni, Ir and combinations thereof. The first metal component may also be selected from a range of metals, but in particular the compounds comprising the first metal component may be selected from the group comprising tungstic acid, molybdic acid, ammonium tungstate, ammonium metatungstate, ammonium paratungstate, tungstate compounds comprising at least one Group 1 or 2 element, metatungstate compounds comprising at least one Group 1 or 2 element, paratungstate compounds comprising at least one Group 1 or 2 element, tungsten oxides, heteropoly compounds of tungsten and various salts and oxides of molybdenum, niobium, vanadium, zirconium, titanium and chromium. The catalyst system according to US 2011/0312488 is stated to improve the selectivity to ethylene glycol and propylene glycol, with a reduced production of butane diols. The ethylene glycol generation is shown in some experiments, indicating that ammonium metatungstate is the preferred first metal component and that as preferred hydrogenation component platinum or nickel may be used. The use of nickel-containing catalyst systems results in the highest yields of ethylene glycol and optionally propylene glycol.

In the above-mentioned article of M. Zheng et al., Chin. J. Catal., 35 (2014) 602-613, the conclusion is drawn that tungsten acid-based catalysts are the most promising candidates for future commercialization of the cellulose-to-ethylene-glycol process. A hydrogenation component is added to such tungsten acid-based catalysts. Examples include ruthenium on activated carbon, but Raney nickel is considered the most promising candidate for commercialization.

The conversion of a carbohydrate to alkylene glycol involves complex reactions. It has been shown in M. Zheng et al., Chin. J. Catal., 35 (2014) 602-613, that lower concentrations of carbohydrate and high reaction temperatures, i.e. above 200° C., are beneficial for the ethylene glycol production. This appears to be confirmed in WO 2014/161852, describing experiments wherein glucose solutions with increasing glucose concentrations, ranging from 1% wt to 6% wt, were contacted with hydrogen in the presence of a catalyst system comprising tungsten and ruthenium. The higher the glucose concentration was, the lower the yield of ethylene glycol became. In order to remedy this disadvantageous effect, it is proposed in WO 2014/161852 to contact a first small portion of the carbohydrate with hydrogen and the catalyst in a solution with a carbohydrate concentration of less than 2% wt, and only when the first portion has reacted, to add further portions of the carbohydrate. In this respect the process is similar to the semi-continuous reactions described in G. Zhao et al., Ind. Eng. Chem. Res., 2013, 52, 9566-9572. Both WO 2014/161852 and G. Zhao et al. in Ind. Eng. Chem. Res., 2013, 52, 9566-9572, mention that, in addition to ethylene glycol, 1,2-butane diol (butylene glycol) is produced. The relative amount of butylene glycol can be in the order of 10%, based on the yield of ethylene glycol. Since butylene glycol and ethylene glycol form an azeotrope, it is difficult to separate the compounds easily via distillation.

The above prior art methods have been conducted in a batch or semi-batch fashion. It would be advantageous to conduct this reaction in a continuous mode. In U.S. Pat. No. 8,410,319 a continuous process is described wherein a cellulose-containing feedstock is contacted with water, hydrogen and a catalyst to generate at least one alkylene glycol. The catalyst comprises a first metal component selected from the group consisting of Mo, W, V, Ni, Co, Fe, Ta, Nb, Ti, Cr, Zr and combinations thereof. The first metal component is in the elemental state or the metal is the carbide, nitride or phosphide compound. The catalyst further comprises Pt, Pd, Ru and combinations thereof, wherein the metal is in the elemental state. The catalyst components are comprised on a carrier. The reactor may be a slurry reactor, an augured reactor system, an immobilized catalyst reaction system having catalyst channels, or an ebullating bed reactor. These reactors are suitable for a three-phase solid/liquid/gas contact. In a slurry reactor the catalyst is suspended in the liquid and the gas is bubbled through the liquid. Thus a slurry reactor is suitable for heterogeneous catalysts. However, the slurry reactor further may have the drawback that the reactor may plug up, and that a high ratio of liquid to catalyst is required. An ebullating bed reactor, also known as a slurry-bed reactor, operates in a similar way, but the catalyst bed is substantially retained in the reactor vessel.

CN102643165 diescribes a continuous process for producing ethylene glycol and propylene glycol from soluble sugars or starch and hydrogen. The catalyst system used contains ruthenium and ammonium metatungstate. In one embodiment the weight ratio of ruthenium to tungsten is 1:1 and the weight ratio of glucose to the sum of ruthenium and tungsten is 150:1. In other embodiments the ratio of tungsten to ruthenium is 5 or 10, and the weight ratio of glucose to the sum of ruthenium and tungsten is 750-800 or 450-460, respectively. After the reaction the effluent is separated. Dissolved tungsten components are recovered and recycled to the reaction. The reaction is conducted in a hydrogenation reactor that is packed with a slurry of a ruthenium on active carbon catalyst and tungsten catalyst. Hydrogen enters from the bottom and stirs the catalyst slurry. The reactor is thus a slurry reactor.

SUMMARY

It has been found that the above-described reactors are less suitable for reactions wherein one or more components of the catalyst dissolves or leaches into the liquid. It has now been found that a continuous stirred tank reactor solves this problem.

Accordingly, the present invention provides a continuous process for preparing ethylene glycol from a carbohydrate source by reaction of the carbohydrate source with hydrogen, wherein hydrogen, the carbohydrate source and a liquid diluent are continuously fed into a continuous stirred tank reactor wherein a catalyst system is present, which catalyst system comprises a tungsten compound and at least one hydrogenolysis metal selected from the groups 8, 9 or 10 of the Periodic Table of the Elements, to achieve the reaction between the carbohydrate source and hydrogen to ethylene glycol;

wherein continuously a product mixture comprising ethylene glycol and diluent is removed from the continuous stirred tank reactor; and wherein continuously or periodically further at least a tungsten compound is added to the continuous stirred tank reactor.

DETAILED DESCRIPTION

The continuous stirred tank reactor (CSTR) is excellently suited for this reaction as through the addition of tungsten the loss of tungsten, which may be by means of the addition of a homogeneous or a heterogeneous tungsten compound, that is leached from the catalyst system in the CSTR is overcome and through the continuous addition of the reactants and continuous removal of the product mixture whilst mechanically stirring the reactants, a steady state situation can be easily created. This allows for a consistent high conversion and high selectivity of the reaction. In this way the amount of tungsten is complemented. Since the hydrogenolysis metal suffers hardly from any leaching there may not be any need to also add additional hydrogenolysis metal to the CSTR. If and to the extent that any hydrogenolysis catalyst is removed from the CSTR during the reaction, such may be complemented by periodical or continuous addition thereof to the CSTR. Further advantages of the use of a CSTR in the present process will become evident later.

The carbohydrate source can be selected from a variety of sources. Suitably, the carbohydrate source comprises or consists of a carbohydrate selected from the group consisting of polysaccharides, oligosaccharides, disaccharides, and monosaccharides. Suitable examples include sustainable sources such as cellulose, hemicellulose, starch, sugars, such as sucrose, mannose, arabinose, glucose and mixtures thereof. Sources that contain the above carbohydrates may include paper pulp streams, municipal waste water streams and other glucose units-containing streams can be used as well, for example from wood waste, paper waste, agricultural waste, municipal waste, paper, cardboard, sugar cane, sugar beet, wheat, rye, barley, other agricultural crops and combinations thereof. These streams may require pre-treatment to remove components that interfere with the current process such as basic fillers, e.g. calcium carbonate in waste paper. In this way the process according to the invention may not only be used from natural sources, but can even be used to upgrade and usefully re-use waste streams. Preferably, the carbohydrate in the carbohydrate source is selected from the group consisting of cellulose, starch, glucose, sucrose, glucose-oligomers, paper waste, and combinations thereof, more preferably glucose or starch. Since cellulose presents difficulties that are absent in other carbohydrate sources, the carbohydrate source is most preferably selected from the group consisting of starch, hemicelluloses and hemicellulose sugars, glucose and combinations thereof.

As shown in the known processes according to the prior art the hydrogenolysis metal can be selected from a wide range of metals. Hydrogenolysis metals may suitably be selected from the group consisting of Cu, Fe, Ni, Co, Pt, Pd, Ru, Rh, Ir, Os and combinations thereof. Preferably, the hydrogenolysis metal is selected from the noble metals Pd, Pt, Ru, Rh, Ir and combinations thereof. It has been found that these metals give good yields. The metal may suitably be present in its metallic form or as its hydride or oxide. It is assumed that the metal oxide will be reduced during the reaction in the presence of hydrogen.

The hydrogenolysis metal or the combination of hydrogenolysis metals is preferably present in the form of a catalyst supported on a carrier. The carrier may be selected from a wide range of known supports. Suitable supports include activated carbon, silica, zirconia, alumina, silica-alumina, titania, niobia, iron oxide, tin oxide, zinc oxide, silica-zirconia, zeolitic aluminosilicates, titanosilicates, magnesia, silicon carbide, clays and combinations thereof. The skilled person will know that activated carbon is an amorphous form of carbon with a surface area of at least 800 m$^2$/g. Such activated carbon thus has a porous structure. Most preferred supports are activated carbon, silica, silica-alumina and alumina, since excellent results have been obtained therewith. More preferably, the catalyst comprises ruthenium as the hydrogenolysis metal and activated carbon as the support.

Suitably, more than one metal is used in the catalyst component comprising the hydrogenolysis metal. Suitably, the combination of hydrogenolysis metals comprises at least one noble metal selected from Pd, Pt, Ru, Rh and Ir in combination with another metal from groups 8, 9 or 10 of the Periodic Table of the Elements. The catalyst, preferably, comprises a mixture of two or more metals of the group consisting of Ru, Pt, Pd, Ir and Rh. Suitable examples are Ru/Ir, Ru/Pt, Ru/Pd. When two metals are used, the weight ratio is suitably in the range of 0.1:1 to 20:1. More preferably, a first hydrogenolysis metal is ruthenium and a second hydrogenolysis metal is selected from Rh, Pt, Pd and Ir. The weight ratio between Ru and the second hydrogenolysis metal is preferably in the range of 0.5:1 to 10:1.

The catalyst system also comprises a tungsten compound. This tungsten compound can be selected from a wide range of compounds. The tungsten may be in the elemental state. Usually, the tungsten compound is then present on a support. Similar to the supports for the at least hydrogenolysis metal, the support may be selected from a wide range of known supports. Suitable supports include active carbon, silica, zirconia, alumina, silica-alumina, titania, niobia, iron oxide, tin oxide, zinc oxide, silica-zirconia, zeolitic aluminosilicates, titanosilicates and combinations thereof. Most preferred are activated carbon, silica, silica-alumina and alumina as support, since excellent results have been obtained therewith. It is also possible to use tungsten compounds in an oxidation state of up to +2, such as in the form of its carbide, nitride or phosphide. Also in this case the tungsten compound may be present in the form of a supported catalyst component. The carrier may be selected from the supports described hereinabove.

Preferably, the tungsten compound has an oxidation state of at least +2, preferably having an oxidation state of +5 or +6. The tungsten compound is then suitably selected from the group consisting of tungstic acid (H$_2$WO$_4$), ammonium tungstate, ammonium metatungstate, ammonium paratungstate, tungstate compounds comprising at least one Group 1 or 2 element, metatungstate compounds comprising at least one Group 1 or 2 element, paratungstate compounds comprising at least one Group 1 or 2 element, tungsten oxide (WO$_3$), heteropoly compounds of tungsten, and combinations thereof. Whereas in the prior art it has been found that certain tungsten compounds leached from their supports and that such was considered a disadvantage, the present inventors have found that it is advantageous to use tungsten compounds that dissolve in the reaction mixture. It has been found that the catalytic activity of the tungsten compound increases if the tungsten compound is dissolved. Without wishing to be bound to any theory it is believed that in the reducing atmosphere that is created in the reaction zone by means of the presence of hydrogen and carbohydrates, hexavalent tungsten compounds may be reduced to pentavalent tungsten and dissolve into the diluent. In this partly reduced state the tungsten ions are effective in attacking the carbon-carbon bonds in the carbohydrate source to form alkylene glycol precursors. It is therefore believed that in the CSTR compounds with tungsten in various oxidation states are present. Such tungsten compounds may include the preferred compounds mentioned hereinabove. Other tungsten compounds may also be feasible. The tungsten compound that is continuously or periodically added to the CSTR is therefore suitably a compound that has an oxidation state of at least +2. More preferably, the tungsten compound that is continuously or periodically added to the CSTR, is selected from the group consisting of tungstic acid (H$_2$WO$_4$), ammonium tungstate, ammonium metatungstate, ammonium paratungstate, tungstate compounds comprising at least one Group 1 or 2 element, metatungstate compounds comprising at least one Group 1 or 2 element, paratungstate compounds comprising at least one Group 1 or 2 element, tungsten oxide (WO$_3$), heteropoly compounds of tungsten, and combinations thereof. A preferred tungsten compound is tungstic acid.

The amount of tungsten that is added to the CSTR is preferably such that the concentration thereof in the CSTR substantially constant. In this specification by substantially constant is understood that the difference between the highest and the lowest amounts of tungsten does not vary more than 10% from the average amount of tungsten in the CSTR. Whereas it is feasible to add tungsten periodically, it is most convenient to provide for a continuous addition of tungsten to the CSTR. The amount added is then suitably adjusted such that it equals the amount of tungsten that is leached from the catalyst system in the CSTR and is removed therefrom with the product mixture. In this way a consistent performance of the CSTR is made possible.

According to the prior art the ratio between the at least one hydrogenolysis metal and the tungsten compound may vary between wide ranges. According to the prior art the weight ratio between these components may vary from 0.02 to 3000. In the present invention the molar ratio of tungsten to the at least one hydrogenolysis metal is preferably in the rather narrow range of 1 to 25. Preferably the molar ratio of tungsten to the at least one hydrogenolysis metal is in the range of 2 to 20, more preferably from 5 to 15. If the ratio is beyond the limits of these ranges, the relative yield of alkylene glycols other than ethylene glycol is decreased and/or the conversion of the carbohydrate is slowed down. Expressed in weight, the weight ratio of tungsten to the at least one hydrogenolysis metal, all calculated as metals, in the CSTR is preferably in the range of 2 to 50 w/w, more preferably from 5 to 50 w/w.

The concentration of the catalyst components may vary in the process according to the present invention. The concentration of the tungsten compound may vary between very wide ranges. The concentration of the tungsten compound according to the prior art batch processes may for instance be selected from the range of 1 to 35% wt, based on the weight of the carbohydrate source introduced into the reaction zone. The amount of hydrogenolysis metal or metals may also vary. It is preferred to apply a higher concentration than what has been disclosed in CN102643165. According to the embodiments of this prior art document the maximum concentration of hydrogenolysis metal, i.e. ruthenium, is 1:300, based on the amount of ruthenium and the amount of carbohydrate introduced into the reactor. In the CSTR reactor that is applied in the process of the present invention the weight ratio of hydrogenolysis metal and carbohydrate that is introduced into the CSTR is preferably in the range of 1:25 to 1:250 wt/wt, preferably from 1:50 to 1:200 wt/wt. Without wishing to be bound by any theory it is believed that at such relatively high concentration of hydrogenolysis metal the formation of humins is avoided and the conversion of carbohydrate to glycols is enhanced. Moreover, the conversion can then be kept at a steady state. In a CSTR at high conversion under steady state conditions the amount of remaining carbohydrate in the reaction mixture is very low. Dependent on the carbohydrate conversion that is set the weight ratio of the tungsten compound, calculated as metal, in the CSTR to the carbohydrate in the CSTR ranges advantageously from 5 to 50 wt/wt. The amount of carbohydrate source in the CSTR is very different from the concentration of the amount of carbohydrate that is being introduced into the CSTR per time unit. The remaining concentration of carbohydrate in the CSTR is much lower. This represents a major difference between the prior art batch and semi-batch processes and the present continuous process. By adjusting the reaction conditions, including the residence time, the skilled person can arrange for a fixed conversion of the carbohydrate source. This conversion will result in a small amount of remaining non-converted carbohydrate in the CSTR. Under steady state conditions this small amount will be kept constant.

The carbohydrate source and the diluent are both introduced into the CSTR. Suitably, the carbohydrate source is introduced together with at least part of the diluent. More preferably, the carbohydrate source is at least partially dissolved in the diluent. Suitably, the diluent is an aqueous medium. Many carbohydrates such as sugars, glucose and fructose are soluble in water. Moreover, cellulose, i.e. a carbohydrate that is regarded as a very suitable starting material, and that is insoluble in water, can be converted into cellodextrins which are water-soluble. Alternatively, the carbohydrate may be introduced into the reaction zone in the form of a slurry. The more common examples of such slurries are aqueous mixtures of water and cellulose and/or starch. In such embodiments aqueous cellulose slurries, containing, e.g. microcrystalline cellulose can suitably be used.

The present process allows for the use of a very concentrated feed stream containing the carbohydrate source. By employing a concentrated feed stream the process economics are benefited. However, it is not necessary to use a concentrated feed stream. Such a feed stream will generally comprise the carbohydrate source and at least part of the diluent. The feed stream comprising the carbohydrate source and diluent suitably has a concentration of 1 to 50% wt, based on the weight of the carbohydrate source and diluent. When a feed stream is employed within this concentration range the feed stream is generally easily transportable. The concentration is not limited to values within this range. The feed stream can e.g. also consist of only carbohydrate source. Typically, such a feed stream is then solid. By introducing the solid carbohydrate into the CSTR at the desired feed rate, the carbohydrate source is dissolved into the reaction mixture and converted.

The prior art processes focus on the conversion of hexoses, such as cellulose, starch and glucose. However, it has been found that it is advantageous to use not only hexose-containing carbohydrates, but also pentose-containing carbohydrates. Therefore the present invention also provides a process wherein the carbohydrate source comprises at least one pentose-containing carbohydrate or, preferably, the carbohydrate source comprises a combination of at least one pentose-containing carbohydrate and at least one hexose-containing carbohydrate. The pentose-containing carbohydrate may be a polysaccharide, an oligosaccharide, a disaccharide or a monosaccharide. The pentose-containing carbohydrate is suitably a pentosan, for instance xylan or arabinan. In particular, it comprises suitably at least one of arabinose, ribose, lyxose and xylose moieties. The application of the process according to the present invention on a combination of hexose- and pentose-containing carbohydrates has the advantage that the pentose-containing carbohydrate yields both propylene glycol and ethylene glycol as main products, and the hexose-containing carbohydrates yield a majority of ethylene glycol. Hence, when propylene glycol is envisaged as a main by-product, the use of pentose-containing carbohydrate as starting material is beneficial. It is evident that the carbohydrate source that comprises hexose and pentose units may be obtained by mixing a separate hexose and a separate pentose fraction. Alternatively, the carbohydrate source may be the product of a natural source that already contains pentose and hexose units. It may e.g. be the hydrolysis product of lignocellulosic biomass, which hydrolysis results in both pentoses and hexoses.

A high concentration of carbohydrate in the diluent may pose problems vis-à-vis the solubility of the carbohydrate source. In order to avoid major problems, water is typically employed as the diluent since carbohydrates tend to be less soluble in most organic diluents. Nevertheless water may optionally partially be replaced by or mixed with organic diluents that have a beneficial effect on the solubility of the any of the reactants or have any other advantage. Accordingly, the diluent comprises one or more of the compounds selected from the group consisting of water, sulfoxides, alcohols, amides and mixtures thereof. Suitably a mixture of water and, optionally, one or more of the above-mentioned organic diluents is used. A suitable sulfoxide is dimethyl sulfoxide (DMSO); suitable examples of amides are dimethyl formamide and dimethyl acetamide. The more preferred organic diluents are the alcohols. The alcohols can be mono-alcohols, in particular water-miscible mono-alcohols, such as $C_1$-$C_4$ alcohols. The alcohol may also be a polyol, e.g. glycerol, xylytol, sorbitol or erythritol. In a particularly preferred embodiment the polyol is a diol. It is most preferred that the organic diluent is an alkylene glycol, such as ethylene glycol, propylene glycol, butylene glycol or a mixture thereof.

The use of alkylene glycol is particularly suitable as it has been found that polyols, including alkylene glycols, facilitate the dissolution of the tungsten compound into the diluent, thereby promoting the catalytic activity of the tungsten compound. It has further been found that the selectivity of the reaction to alkylene glycols is enhanced by the use of alkylene glycol as component in the diluent. Without being wished to be bound by any theory it is believed that tungsten forms complexes with alkylene glycol whereby the conversion to by-products is reduced. Moreover, the use of an alkylene glycol as diluent does not involve the introduction of an extraneous reagent into the reaction mixture, which represents a further advantage. Since alkylene glycols tend to facilitate the solubility of the tungsten compound it is advantageous to introduce tungsten periodically or continuously into the CSTR together with an alkylene glycol. That entails the advantage that the dosing of the desired amount of tungsten can be easily accomplished. Further, since the reaction produces alkylene glycols, in particular ethylene glycol, the alkylene glycol addition does not introduce an extraneous compound into the CSTR. Preferably, tungsten is introduced into the CSTR together with ethylene glycol. Such an alkylene glycol for use as diluents component may be obtained form the reaction. Hence a portion of the alkylene glycols that are produced in the process of the present invention may be recycled to the CSTR as diluents for the carbohydrate and/or tungsten catalyst component.

As indicated above, the ethylene glycol-containing product of the process according to the present invention generally is a mixture of alkylene glycols. This mixture is suitably purified, especially when pure ethylene glycol is desired for polymerization purposes. The azeotrope that is formed with butylene glycol makes it difficult to obtain pure ethylene glycol.

To facilitate the separation process it is advantageous to use pentose-containing carbohydrate as starting material, alone or in addition to hexose-containing carbohydrate. Pentose-containing carbohydrates form hardly any butylene glycol as by-product. Hence, the proportion of butylene glycol in the reaction product of a combination of pentose- and hexose-containing carbohydrates will be relatively small. The purification of such a reaction product is therefore relatively simple. Propylene glycol and ethylene glycol can be easily separated from each other by means of fractionation. Fractionation of the product of the reaction with a starting material that comprises both pentose- and hexose-containing carbohydrates will result in pure ethylene glycol, pure propylene glycol and a relatively small fraction containing butylene glycol with one or both of the other glycols.

Another method of removing butylene glycol from the products would be by using one or more entraining agents. The entraining agent selectively removes butylene glycol from a mixture of alkylene glycols by means of azeotropic distillation. Such a procedure can be applied to processes wherein the starting material comprises only hexose-containing carbohydrates, only pentose-containing carbohydrates or a combination of both. The entraining agent can suitably be selected from the group consisting of the entrainers selected from ethyl benzene, p-xylene, n-propyl benzene, o-diethyl benzene, m-diethyl benzene, m-di-isopropyl benzene, cyclopentane, methyl cyclohexane, 3-methyl pentane, 2,3-dimethyl butane, heptane, 1-heptene, octane, 1-octene, 2,3,4-trimethyl pentane, decane, methyl ethyl ketoxime, decalin, dicyclo pentadiene, alpha-phellandrene, beta-pinene, myrcene, terpinolene, p-mentha-1,5-diene,3-carene, limonene and alpha-terpinene.

In addition, higher polyols, such as glycerol, erythritol, or sorbitol may function as an entraining agent. These compounds tend to be produced as by-products in the process for preparing ethylene glycol from carbohydrates, as shown in M. Zheng et al., Chin. J. Catal., 35 (2014) 602-613. These compounds may therefore be recycled to the process. If necessary, one or more of these compounds can also be added to the product of the present process in order to enhance their concentrations and facilitate thereby the obtaining of pure ethylene glycol, when they are used as entraining agents.

In another process for the production of pure ethylene glycol the product mixture comprising ethylene glycol, propylene glycol and butylene glycol can be converted with a carbonyl group-containing compound to form a mixture of dioxolanes. These dioxolanes do not form azeotropes and therefore can be separated relatively easily by means of distillation. After having obtained the pure dioxolanes as separate fractions, each fraction can be hydrolyzed to yield the pure corresponding alkylene glycol. The carbonyl group-containing compound suitably is an aldehyde or ketone. It preferably has a boiling point of at least 100° C., so that any water that is introduced in the reaction can be easily separated from the reaction product. Another way to enable an easy separation between water and the dioxolanes is by selecting the carbonyl group-containing compound such that at least some of the resulting dioxolanes are not soluble in water. In this way the resulting dioxolanes may be separated from water by phase separation. By doing so any water soluble by-product is also separated from the dioxolanes. One way to achieve that is by selecting a carbonyl group-containing compound that is insoluble in water itself. Very convenient carbonyl group-containing compounds include methyl isobutyl ketone, t-butyl methyl ketone and mixtures thereof. These compounds have a suitable boiling point in the range of 106 to 118° C. and they are insoluble in water. The dioxolanes formed with these compounds are also insoluble in water so that separation of these compounds from water is facilitated.

The reaction of the carbonyl group-containing compound with the alkylene glycols in the product can be catalyzed by means of a catalyst. A suitable catalyst includes an acid catalyst. Although homogeneous acid catalysts may be used, they have the drawback that the neutralization and/or separation may become cumbersome. Therefore, the acid catalyst is suitably a solid acid catalyst, preferably selected from acidic ion exchange resins, acid zeolites and combinations thereof. The use of a solid product also facilitates the contact between the liquid alkylene glycol mixture and the carbonyl group-containing compound when the dioxolane formation is carried out in a stripping column reactor, wherein a vapor of the carbonyl group containing compound is contacted in counter current with a liquid stream of the alkylene glycol mixture when this mixture is passed along the solid acid catalyst. However, it is also feasible to include a homogeneous acid catalyst in the product mixture and pass the vapor of the carbonyl group-containing compound through this liquid mixture.

When the dioxolanes have been formed they can be easily separated from each other by distillation. After distillation the separate dioxolanes can be hydrolyzed to form pure ethylene glycol. The hydrolysis of the dioxolanes is suitably also catalyzed by means of an acid catalyst. The hydrolysis may be achieved in a similar way as to the formation of the dioxolanes, e.g. by contacting a liquid stream of the dioxolane with a vaporous stream of water counter-currently. The acid catalyst may be included in the dioxolane liquid or may be provided as a solid acid catalyst. The acid catalyst included in the dioxolane liquid may be a strong organic acid, such as p-toluene sulfonic acid or methane sulfonic acid. Preferably the catalyst is a solid catalyst comprising an acid ion exchange resin, an acid zeolite or a combination thereof.

As indicated above the product mixture also comprises tungsten, that is leached from a heterogeneous catalyst system or that results from the addition of a homogeneous tungsten compound. It is desirable to reclaim the tungsten from the product mixture. This can typically be accomplished when the distillation steps to remove various alkylene glycols from the product mixture has been conducted, and a distillation residue is obtained. Tungsten may then be recovered by complexation with a polymer, such as polyquaternium-6, and subsequent ultrafiltration, as described in Chin. J. Chem. Eng., 20(2012) 831-836. Alternatively, at least part of the distillation residue may be acidified, e.g. with nitric acid, to provoke the precipitation of tungstic acid.

The tungsten compound reclaimed can suitably be recycled to the CSTR. It is also possible to recycle the tungsten by means of at least part of the distillation residue without separate recovery and isolation of the tungsten compound. In such a case it may be desirable to remove various alcohols and other by-products from the distillation residue before the remaining part is recycled to the CSTR.

The process for the preparation of an alkylene glycol according to the present invention can be carried out under the process conditions that are broadly known in the art. The conditions include those that are disclosed in WO 2014/161852. Hence, the reaction temperature is suitably at least 120° C., preferably at least 140° C., more preferably at least 150° C., most preferably at least 160° C. The temperature in the reactor is suitably at most 300° C., preferably at most 280° C., more preferably at most 270° C., even more preferably at most 250° C., and most preferably at most 200° C. The reactor may be brought to a temperature within these ranges before addition of any starting material and is maintained at a temperature within the range.

It has been found that the process according to the present invention more advantageously is carried out at temperatures that are generally somewhat lower than those used in the prior art processes. It has been found that the formation of butylene glycol is reduced if relatively low temperatures are employed. The more advantageous temperature range is from 150 to 225° C., more preferably from 160 to 200° C., and most preferably from 165 to 190° C. This is contrary to what is taught in U.S. Pat. No. 7,960,594 wherein a reaction temperature in the range 220-250° C. was stated to be most useful.

The process of the present invention takes place in the presence of hydrogen. The hydrogen can be supplied as substantially pure hydrogen. The total pressure will then be the hydrogen pressure. Alternatively, the hydrogen may be supplied in the form of a mixture of hydrogen and an inert gas. The total pressure will then consist of the partial pressures of hydrogen and this inert gas. The inert gas can suitably be selected from nitrogen, argon, helium, neon and mixtures thereof. The ratio of hydrogen to the inert gas may vary between wide ranges. Suitably, the ratio is not very low, since the reaction proceeds well when the hydrogen partial pressure is sufficiently high. Accordingly, the volume ratio between hydrogen and the inert gas may be from 1:1 to 1:0.01. More preferably, only hydrogen is used as gas in the process according to the invention.

Hydrogen is typically supplied via a distributor, e.g. a sparger, to the CSTR. Via this distributor and through the stirring mechanism hydrogen is dissolved in the reaction mixture, thereby enabling the reaction of hydrogen with the carbohydrate in the presence of the catalyst system. Hydrogen is maintained in the CSTR under pressure. The hydrogen pressure is suitably maintained at the desired level. Apart from any gas, such as hydrogen, entrained with the product mixture no other gases leave the CSTR.

The pressure in the CSTR is suitably at least 1 MPa, preferably at least 2 MPa, more preferably at least 3 MPa. The pressure in the CSTR is suitably at most 16 MPa, more preferably at most 12 MPa, more preferably at most 10 MPa. The skilled person will understand that the pressure at 20° C. will be lower than the actual pressure at the reaction temperature. The pressure applied in the process is suitably 0.7 to 8 MPa, determined at 20° C. The pressure may be applied by hydrogen gas or a hydrogen-containing gas. When a hydrogen-containing gas is used, the hydrogen content in the hydrogen-containing gas is suitably up to 100 vol %, preferably pure hydrogen. The balance of any hydrogen-containing gas may suitably be an inert gas, such as nitrogen, helium, neon, argon or mixtures thereof. When the hydrogen is subsequently heated in the CSTR the pressure at reaction is suitably in the range of 1 to 16 MPa. As the reaction proceeds some hydrogen is consumed. Due to the continuous supply of hydrogen the hydrogen partial pressure is suitably kept substantially constant. Advantageously, the hydrogen partial pressure at reaction temperature is maintained within the range of 1 to 6 MPa.

The reaction time in the process according to the present invention may vary. Suitably the residence time of the carbohydrate source is at least 1 min. Preferably the residence time is in the range of 5 min to 6 hrs, more preferably from 5 min to 2 hr. In the present continuous process the residence time is understood to be the quotient of the mass flow rate of the carbohydrate source into the reaction zone divided by the mass flow rate of the catalyst system in the reaction zone. Generally the continuous process is operated at a weight hourly space velocity (WHSV), expressed as the mass of carbohydrate source per mass of hydrogenolysis metal, expressed as metal, per hour, in the range of 0.01 to 100 $hr^{-1}$, preferably from 0.05 to 10 $hr^{-1}$.

When the product mixture is removed from the CSTR it may be subjected to purification to isolate the desired ethylene glycol and/or other by-products and/or tungsten. When the conversion in the CSTR has been set to a level wherein the product mixture contains an amount of non-converted carbohydrate source that is to be used, it is feasible to feed the product mixture into a further reactor where at least the carbohydrate source in the product mixture is contacted with a further catalyst. Such a catalyst may be the same or similar to the catalyst system used in the CSTR. The further reactor may be selected from any type of reactor, including a plug flow reactor, a slurry reactor, an ebullating bed reactor or another CSTR.

The invention is illustrated by means of the following example.

Example 1

A CSTR provided with a stirrer and having a volume of 3.5 ml was filled with 100 mg of a hydrogenolysis catalyst comprising 5% wt ruthenium on active carbon. A feedstock comprising 5% wt glucose in a mixture of water and glycerol (82% wt water and 18% wt glycerol), based on the weight of the mixture, was fed into the CSTR. The feedstock further comprised 0.8 g sodium hydroxide per liter of the mixture. The feedstock flow also contained 1% wt tungstic acid ($H_2WO_4$). The reaction temperature was kept at 200° C., the hydrogen pressure was 50 bar, and the stirrer speed was 1000 rpm. The weight ratio of tungsten to ruthenium in the experiment was 2.2 wt/wt. The weight ratio of ruthenium to glucose introduced into the CSTR was 1:115. The flow of liquid feedstock was 0.15 ml/min, and the hydrogen flow was 100 ml/min. The residence time of the liquid in the reactor was therefore about 23.3 min. It appeared that the conversion of glucose was constant at about 98.5%. The effluent was analyzed and the selectivities towards ethylene glycol (sEG), propylene glycol (sPG) and butylene glycol (sBG) were determined. The selectivities were calculated as the amounts of ethylene glycol, propylene glycol and butylene glycol were determined, calculated as the weight percentage in the reactor effluent divided by the amount of grams glucose being introduced into the CSTR.

The results of the experiment at different run times are shown in Table 1 below.

TABLE 1

| Run time, h | sEG | sPG | sBG |
|---|---|---|---|
| 3 | 41.7 | 3.8 | 1.8 |
| 4 | 46.0 | 3.8 | 1.8 |
| 5 | 45.8 | 3.8 | 2.0 |
| 6 | 47.0 | 3.7 | 2.4 |
| 7 | 49.7 | 4.1 | 2.8 |

The results show that the process yields excellent consistent selectivities towards the desired alkylene glycols, in particular towards ethylene glycol.

Example 2

To show the effect of the catalyst concentration and the effect of the glucose concentration experiments were run in the same way as those in Example 1, with the exception that in one experiment the amount of ruthenium catalyst was 50 mg instead of 100 mg. Thereby the W/Ru ratio changed to 4.2 wt/wt and the weight ratio of ruthenium to glucose introduced into the CSTR was 1:230.

In another experiment the glucose concentration was set at 2.5% wt. The W/Ru ratio was 2.2 wt/wt and the weight ratio of ruthenium to glucose introduced into the CSTR was 1:115.

In addition to the selectivities, also the glucose conversion is reported. The results are shown in Table 2.

TABLE 2

| Ru, mg | Glucose conc., % wt | Run time, h | Conversion, % | sEG | sPG | sBG |
|---|---|---|---|---|---|---|
| 50 | 5 | 2 | 94.6 | 30.0 | 3.4 | 6.4 |
| 50 | 5 | 3 | 92.8 | 21.8 | 1.6 | 3.7 |
| 50 | 5 | 4 | 90.9 | 14.6 | 0.7 | 1.8 |
| 50 | 5 | 6 | 89.8 | 9.4 | 0.0 | 0.9 |
| 50 | 5 | 7 | 89.3 | 6.6 | 0.0 | 0.5 |
| 100 | 2.5 | 3 | 98.9 | 51.2 | 0.1 | 2.1 |
| 100 | 2.5 | 4 | 99.2 | 60.1 | 0.1 | 2.9 |
| 100 | 2.5 | 5 | 99.3 | 53.5 | 0.1 | 4.0 |
| 100 | 2.5 | 6 | 99.2 | 56.7 | 0.1 | 5.2 |

The results show that at a reduced ruthenium content the selectivities towards the alkylene glycols decrease over time. It appears that humins are formed which accelerate the deactivation of the ruthenium catalyst. Accordingly, also the glucose conversion decreases over time.

At a reduced glucose concentration the conversion is substantially complete. The selectivity towards ethylene glycol is excellent. The selectivity towards butylene glycol increases over time. When butylene glycol is considered undesirable, it is therefore advantageous to work at higher carbohydrate concentrations.

The invention claimed is:
1. Continuous process for preparing ethylene glycol from a carbohydrate source by
reaction of the carbohydrate source with hydrogen,
wherein hydrogen, the carbohydrate source and a liquid diluent are continuously fed into a continuous stirred tank reactor wherein a catalyst system is present, which catalyst system comprises a tungsten compound and at least one hydrogenolysis metal selected from the groups 8, 9 or 10 of the Periodic Table of the Elements, to achieve the reaction between the carbohydrate source and hydrogen to ethylene glycol;
wherein continuously a product mixture comprising ethylene glycol and diluent is removed from the continuous stirred tank reactor; and
wherein continuously or periodically further at least a tungsten compound is added to the continuous stirred tank reactor (CSTR), wherein the amount of tungsten that is added to the CSTR is such that the concentration thereof in the CSTR is substantially constant.

2. Continuous process according to claim 1, wherein the weight ratio of tungsten to the at least one hydrogenolysis metal, all calculated as metals, in the CSTR is in the range of 2 to 50 wt/wt.

3. Continuous process according to claim 1, wherein the weight ratio of tungsten calculated as metal to carbohydrate source in the CSTR is in the range of 5 to 50 wt/wt.

4. Continuous process according to claim 1, wherein the tungsten compound that is continuously or periodically added to the CSTR has an oxidation state of at least +2.

5. Continuous process according to claim 1, wherein the weight ratio of the at least one hydrogenolysis metal and carbohydrate that is introduced into the CSTR is in the range of 1:25 to 1:250 wt/wt.

6. Continuous process according to claim 1, wherein the tungsten compound that is continuously or periodically added to the CSTR, is selected from the group consisting of tungstic acid ($H_2WO_4$), ammonium tungstate, ammonium metatungstate, ammonium paratungstate, tungstate compounds comprising at least one Group 1 or 2 element, metatungstate compounds comprising at least one Group 1 or 2 element, paratungstate compounds comprising at least one Group 1 or 2 element, tungsten oxide ($WO_3$), heteropoly compounds of tungsten, and combinations thereof.

7. Continuous process according to claim 1, wherein the hydrogenolysis metal from groups 8, 9 or 10 of the Periodic Table of the Elements is selected from the group consisting of Cu, Fe, Ni, Co, Pd, Pt, Ru, Rh, Ir, Os and combinations thereof.

8. Continuous process according to claim 1, wherein the at least one hydrogenolysis metal from the groups 8, 9 or 10 of the Periodic Table of the Elements is present in the form of a catalyst supported on a carrier.

9. Continuous process according to claim 8, wherein the carrier is selected from the group supports, consisting of activated carbon, silica, alumina, silica-alumina, zirconia, titania, niobia, iron oxide, tin oxide, zinc oxide, silica-zirconia, zeolitic aluminosilicates, titanosilicates, magnesia, silicon carbide, clays and combinations thereof.

10. Continuous process according to claim 7, wherein the catalyst system comprises ruthenium on activated carbon.

11. Continuous process according to claim 1, wherein the carbohydrate source comprises a combination of at least one pentose-containing carbohydrate and at least one hexose-containing carbohydrate.

12. Continuous process according to claim 1, wherein the rate of addition of the carbohydrate source into the CSTR is such that WHSV is in the range of 0.01 to 100 $hr^{-1}$.

13. Continuous process according to claim 1, wherein the diluent is selected from water and, optionally, one or more of the organic diluents sulfoxides, alcohols and amides.

14. Continuous process according to claim 13, wherein the organic diluent is an alcohol.

15. Continuous process according to claim 13, wherein the organic diluent is an alkylene glycol.

16. Continuous process according to claim 1, wherein the temperature in the reaction zone ranges from 120 to 300° C.

17. Continuous process according to claim 1, wherein the hydrogen partial pressure in the reaction zone is in the range of 1 to 6 MPa.

18. Continuous process according to claim 13, wherein the organic diluent is ethylene glycol.

19. Continuous process according to claim 1, wherein the temperature in the reaction zone ranges from 150 to 225° C.

20. Continuous process according to claim 1, wherein the amount of tungsten that is added to the CSTR is such that the difference between the highest and the lowest amounts of tungsten in the CSTR do not vary more than 10% from the average amount of tungsten in the CSTR.

21. Continuous process for preparing ethylene glycol from a carbohydrate source by
   reaction of the carbohydrate source with hydrogen,
   wherein hydrogen, the carbohydrate source and a liquid diluent are continuously fed into a continuous stirred tank reactor wherein a catalyst system is present, which catalyst system comprises a tungsten compound and at least one hydrogenolysis metal selected from the groups 8, 9 or 10 of the Periodic Table of the Elements, to achieve the reaction between the carbohydrate source and hydrogen to ethylene glycol;
   wherein continuously a product mixture comprising ethylene glycol and diluent is removed from the continuous stirred tank reactor; and
   wherein continuously or periodically further at least a tungsten compound is added to the continuous stirred tank reactor (CSTR), wherein the tungsten compound is dissolved into the diluent and the diluent comprises a polyol.

22. Continuous process according to claim 21, wherein the tungsten compound is introduced periodically or continuously into the CSTR together with an alkylene glycol.

23. Continuous process according to claim 22, wherein the alkylene glycol is ethylene glycol, propylene glycol, butylene glycol or a mixture thereof.

24. Continuous process according to claim 22, wherein the alkylene glycol is ethylene glycol.

\* \* \* \* \*